United States Patent
Engman et al.

(10) Patent No.: US 12,115,378 B2
(45) Date of Patent: *Oct. 15, 2024

(54) WCD USER INTERFACE RESPONSE TO A CHANGE IN DEVICE ORIENTATION

(71) Applicant: WEST AFFUM HOLDINGS DAC, Dublin (IE)

(72) Inventors: Zoie R. Engman, Kirkland, WA (US); Aaron J. Piazza, Lake Forest Park, WA (US); Erick M. Roane, Kirkland, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/717,322

(22) Filed: Apr. 11, 2022

(65) Prior Publication Data

US 2022/0233873 A1 Jul. 28, 2022

Related U.S. Application Data

(63) Continuation of application No. 16/394,565, filed on Apr. 25, 2019, now Pat. No. 11,298,556.

(Continued)

(51) Int. Cl.
*A61N 1/00* (2006.01)
*A61N 1/04* (2006.01)
*A61N 1/39* (2006.01)

(52) U.S. Cl.
CPC ........... *A61N 1/3904* (2017.08); *A61N 1/046* (2013.01); *A61N 1/3912* (2013.01);
(Continued)

(58) Field of Classification Search
CPC .... A61N 1/3904; A61N 1/046; A61N 1/3912; A61N 1/3925; A61N 1/3968; A61N 1/3975; A61N 1/3993
See application file for complete search history.

(56) References Cited

U.S. PATENT DOCUMENTS

| | | |
|---|---|---|
| 3,724,355 A | 4/1973 | Busch et al. |
| 4,583,524 A | 4/1986 | Hutchins |

(Continued)

FOREIGN PATENT DOCUMENTS

| | | |
|---|---|---|
| DE | 2005060985 A2 | 6/2007 |
| EP | 2305110 A1 | 4/2011 |

(Continued)

OTHER PUBLICATIONS

Heartstart MRx and XL AED Algorithm-Application Note, Jul. 2001, Edition 2 Philips Healthcare, USA.

(Continued)

*Primary Examiner* — Scott M. Getzow
(74) *Attorney, Agent, or Firm* — Polsinelli PC

(57) ABSTRACT

In one embodiment, a wearable cardioverter defibrillator (WCD) is described. The WCD includes a support structure worn by a patient. A processor is coupled to the support structure. The WCD also includes a discharge circuit coupled to an energy storage module, the discharge circuit configured to discharge the stored electrical charge through a body of the patient. The wearable cardioverter defibrillator also includes a user interface housing at least one sensor and responsive to changes in device orientation. The processor is configured to detect a motion at the user interface and determine when the motion is patient-activated. When the motion is patient-activated, the processor determines a direction of rotation. The processor determines an orientation of a display at the user interface based on the direction of rotation and orients the display at the user interface to appear upright to the patient.

20 Claims, 7 Drawing Sheets

Related U.S. Application Data

(60) Provisional application No. 62/662,472, filed on Apr. 25, 2018.

(52) U.S. Cl.
CPC ......... *A61N 1/3925* (2013.01); *A61N 1/3968* (2013.01); *A61N 1/3975* (2013.01)

(56) References Cited

U.S. PATENT DOCUMENTS

| | | | |
|---|---|---|---|
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,618,208 A | 4/1997 | Crouse et al. | |
| 5,662,690 A | 9/1997 | Cole et al. | |
| 5,674,249 A * | 10/1997 | de Coriolis | A61N 1/3925 128/903 |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,265,432 B2 | 2/2016 | Warren et al. | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,721,375 B1 | 8/2017 | Rivard | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 2002/0181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0001943 A1 | 1/2012 | Ishidera | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0245161 A1 | 8/2014 | Yuen et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2015/0331996 A1 | 11/2015 | Gustavson et al. | |
| 2016/0004831 A1 | 1/2016 | Carlson et al. | |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0256104 A1 | 9/2016 | Romem et al. | |
| 2016/0283900 A1 | 9/2016 | Johnson et al. | |
| 2017/0014073 A1 | 1/2017 | Shoshani et al. | |

(56) References Cited

U.S. PATENT DOCUMENTS

| | | |
|---|---|---|
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0243327 A1* | 8/2017 | Zhang .................. G06T 3/60 |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | |
|---|---|---|
| JP | 4320257 A | 3/2005 |
| JP | 5963767 A | 1/2014 |
| JP | 2014526282 A | 10/2014 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

WCD USER INTERFACE RESPONSE TO A CHANGE IN DEVICE ORIENTATION

CROSS-REFERENCE TO RELATED APPLICATION

This application is a continuation of U.S. application Ser. No. 16/394,565, filed Apr. 25, 2019, which claims priority from U.S. Provisional Application No. 62/662,472, filed Apr. 25, 2018, the disclosures of which are hereby incorporated by reference herein in their entirety for all purposes.

BACKGROUND

Heart arrhythmias may reduce blood flow to various parts of the body. In some instances, arrhythmias result in a Sudden Cardiac Arrest (SCA) where a person's heart suddenly and unexpectedly stops beating. If this occurs, blood may stop flowing to the brain and other vital organs. SCA can lead to death very quickly, within minutes, unless action is taken quickly.

Some people have an increased risk of SCA. This includes people who have had a heart attack, a prior SCA episode, among other risk factors. Frequently, these people are recommended for an Implantable Cardioverter Defibrillator ("ICD"). The ICD is a small electronic device connected to the heart that continuously monitors the person's electrocardiogram ("ECG"). If or when the ICD detects certain types of heart arrhythmias or abnormalities, then the ICD delivers an electric pulse or shock to the heart.

A patient may have a period of time between being recommended for an ICD and actually receiving one. In the interim timeframe, a patient may be suited with a wearable cardioverter defibrillator ("WCD") system. A WCD system is worn by the patient and includes, among other components, a defibrillator and one or more external electrodes. When a patient wears a WCD system, the WCD may monitor several patient parameters, including the patient's ECG. If a potentially life-threatening arrhythmia is detected, then the defibrillator may be activated and primed to deliver an appropriate electric shock through the patient's body which also shocks the heart.

When a patient is given a WCD, the patient typically must interact with the system to ensure the system is functioning properly, to receive input and stats from the WCD, and to provide feedback when needed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, a wearable cardioverter defibrillator (WCD) is described. The WCD includes a support structure configured to be worn by a patient. A processor is coupled to the support structure and an energy storage module configured to store an electrical charge is in communication with the processor. The wearable cardioverter defibrillator also includes a discharge circuit coupled to the energy storage module, the discharge circuit in communication with the processor and configured to discharge the stored electrical charge through a body of the patient. The wearable cardioverter defibrillator also includes a user interface housing at least one sensor and responsive to changes in device orientation. The processor is configured to detect a motion at the user interface and determine when the motion is patient-activated. When the motion is patient-activated, the processor determines a direction of rotation. The processor determines an orientation of a display at the user interface based on the direction of rotation and orients the display at the user interface to appear upright to the patient.

In some embodiments, the processor is further configured to determine when the motion passes an angular threshold from a baseline plane of the user interface. In some embodiments, the angular threshold is between about 30 and about 60 degrees from the baseline plane. In further embodiments, the angular threshold is approximately 45 degrees from the baseline plane. In some embodiments, the processor is further configured to determine a direction of motion of the user interface. In some embodiments, the direction of motion may be one of clockwise or counterclockwise. In some examples, the at least one sensor includes one or more of an accelerometer, gyroscope, or a combination thereof. In some embodiments, the processor is further configured to illuminate a visual status indicator when the motion is patient-activated. In some embodiments, the processor is further configured to activate the user interface when the motion is patient-activated. In one embodiment, the processor is further configured to determine a lateral location of the user interface on the patient and orient content of the user interface to accommodate for the lateral location of the user interface.

In another embodiment, a WCD system is described. The WCD may include a support structure for wearing by a patient. A defibrillator housing is coupled to the support structure. A discharge circuit is in communication with the defibrillator housing, the discharge circuit configured to discharge a stored electrical charge through a body of the patient. The wearable cardioverter defibrillator also includes a communication device coupled to the support structure, the communication device configured to communicate a status of the WCD to the patient. The wearable cardioverter defibrillator also includes a user interface coupled to the communication device, the user interface configured to respond to changes in orientation. The wearable cardioverter defibrillator also includes at least one motion sensor coupled to the user interface, the motion sensor positioned to detect a movement of the user interface. The processor is configured to detect a motion at the user interface and determine when the motion is patient-activated. When the motion is patient-activated, the processor determines a direction of rotation. The processor determines an orientation of a display at the user interface based on the direction of rotation and orients the display at the user interface to appear upright to the patient.

In another embodiment, a WCD system is described. The WCD may include a support structure for wearing by a patient; one or more electrodes for delivering a charge to the patient, while the patient is wearing the support structure. A discharge circuit may be coupled to the electrodes, the discharge circuit configured to store an electrical charge. The WCD may include a processor for activating the discharge circuit, the processor in communication with the discharge circuit. A communication device may be coupled to the support structure, the communication device configured to communicate a status of the WCD to the patient. A user interface may be coupled to the communication device, the user interface configured to respond to changes in orientation. At least one motion sensor may be coupled to the user interface, the motion sensor configured to monitor a motion parameter of the patient while the patient wears the communication device and to transmit a motion parameter.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCD) are worn by patients at risk for sudden cardiac arrest. When a patient wears a WCD, the patient, and sometimes a third party, may interact with the device for various reasons throughout the day and night. For example, the WCD may have an alarm and vibration alert to perform a consciousness test. If the patient is conscious, the patient may engage with the WCD to deactivate the alarm and prevent any further action. If the patient is unconscious, a third party may interact with the WCD to ensure its proper function and shock capabilities are activated. In another example, the patient may wish to monitor their heart rate and other health parameters via the WCD throughout the day. For example, the patient may be exercising or performing a strenuous task and may wish to check their pulse and heartrate. The patient may also periodically check the WCD system to ensure the components are properly attached to the patient and functioning. In any situations, either the patient or a third party may need to interact with, provide feedback to, or receive data from the WCD. A graphical user interface (GUI) may provide that information but may not always be user friendly. The GUI may not respond to changes in orientation, haptic feedback, or other information. This may make it difficult for the patient, or a third party to interact with the WCD.

Figure 1:
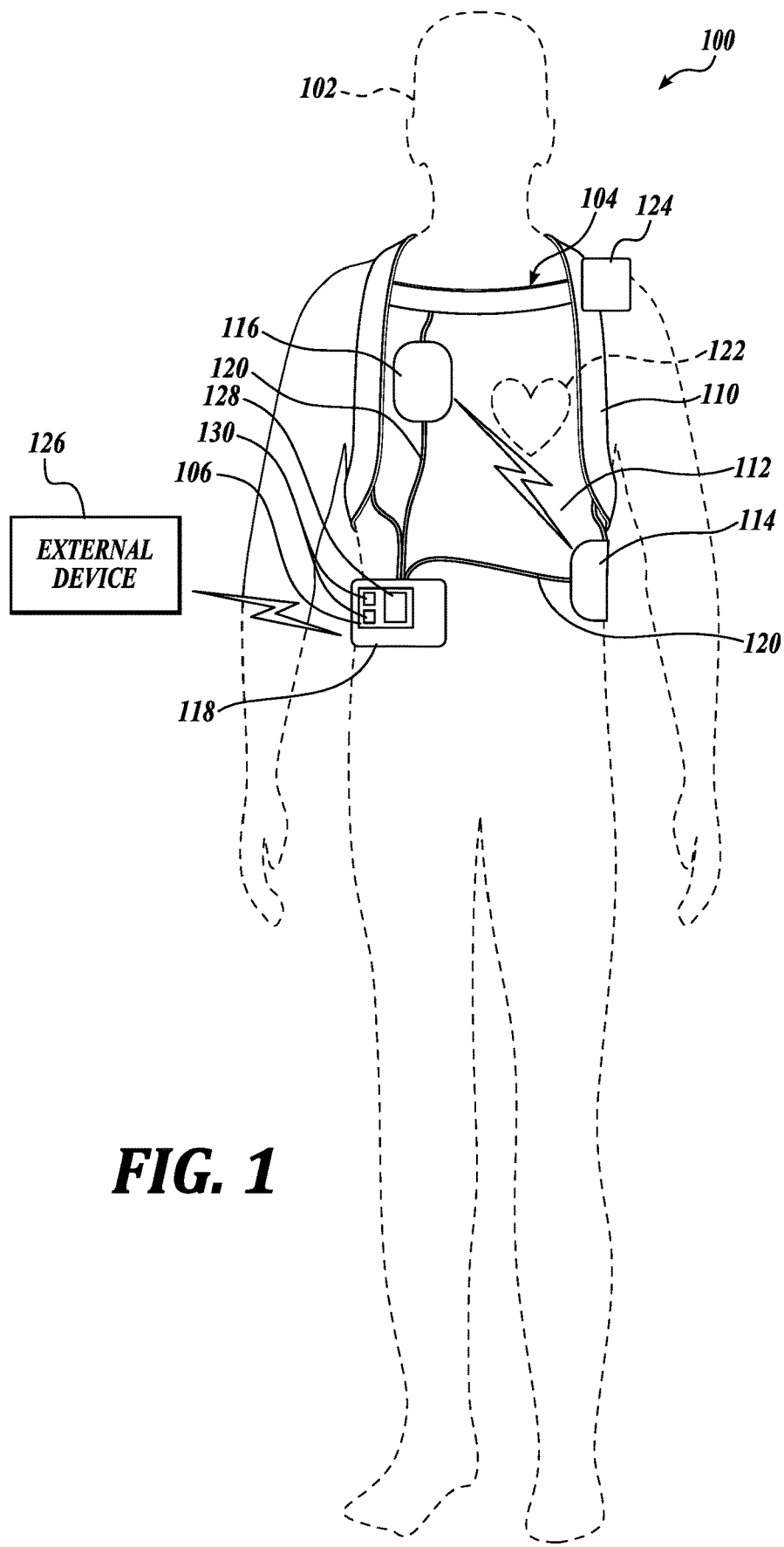
FIG. 1 is a diagram of a sample WCD system in accordance with the present disclosure.

FIG. 1 illustrates a system with a patient 102 wearing an example of a WCD system 104 according to embodiments described herein. The WCD system may include a communication device 106, a support structure 110, an external defibrillator 118 connected to defibrillation electrodes 114, 116, among other components.

The support structure 110 may be worn by the patient 102. The support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component support structure 110 may additionally carry or couple to the various components of the WCD system 104.

In other embodiments, the support structure 110 may comprise multiple components. For example, the support structure 110 may include a first component resting on a patient's shoulders. The first component may locate a series of defibrillation electrodes 114, 116 on the torso 112 of the patient 102. A second component may rest more towards the patient's hips, whereby the second component may be positioned such that the patient's hips support the heavier components of the WCD system 104. In some embodiments, the heavier components of the WCD system 104 may be carried via a shoulder strap, or may be kept close to the patient 102 such as in a cart, bag, stroller, wheel chair, or other vehicle.

The external defibrillator 118 may be coupled to the support structure 110 or may be carried remotely from the patient 102. The external defibrillator 118 may be triggered to deliver an electric shock to the patient 102 when patient 102 wears WCD system 104. For example, if certain thresholds are exceeded or met, the external defibrillator 118 may be engaged and deliver a shock to the patient 102.

The WCD system 100 may defibrillate the patient 102 by delivering an electrical charge to the patient 102 through a series of electrodes 114, 116 positioned on the torso 112. The electrodes 114, 116 may be electrically coupled to the external defibrillator 118 via a series of electrode leads 120. The defibrillator 118 may administer an electric shock to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116. The electric shock may be a defibrillation shock, which may go through a heart 122 of the patient 102 in an attempt to restart the heart 122. The brief, strong electric pulse may work to restart the heart 122 which may save the patient's life.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include physical state of the patient 102 such as ECG, movement, heartrate, pulse, temperature, and the like. Local parameters may also include a parameter of the WCD 104, environmental parameters, or the like. The monitoring device 124 may be physically coupled to the support structure 110 or may be proximate the support structure 110. In either location, the monitoring device 124 is communicatively coupled with other components of the WCD 104.

In some embodiments, the WCD system 104 may include a communication device 106 to enable the patient to interact with, and garnish data from, the WCD system 104. The communication device 106 may be a part of the defibrillator 118 or may be a separate device. The communication devices 106 may include a screen 128 and one or more user inputs 130 to enable the patient to interact with the WCD system 104. In some embodiments, the patient may view patient data, dismiss a shock if the patient is still conscious, turn off an alarm, and otherwise engage with the WCD system 104 via the communication device 106. The communication device 106 may be wired, or wirelessly linked to the external defibrillator 118 and may be removable from the defibrillator 118 or a separate component. In some embodiments, the communication device 106 may form an inseparable assembly and share internal components with the defibrillator 118.

In some embodiments, the communication device 106 or the defibrillator 118 may connect with one or more external devices 126. For example, as shown in FIG. 1, the communication device 106 or the defibrillator 118 may connect to various external devices 126 such as a cloud computing network, a remote desktop, a laptop, a mobile device, or other external device using a network such as the Internet, local area networks, wide area networks, virtual private networks (VPN), other communication networks or channels, or any combination thereof.

Figure 2A:
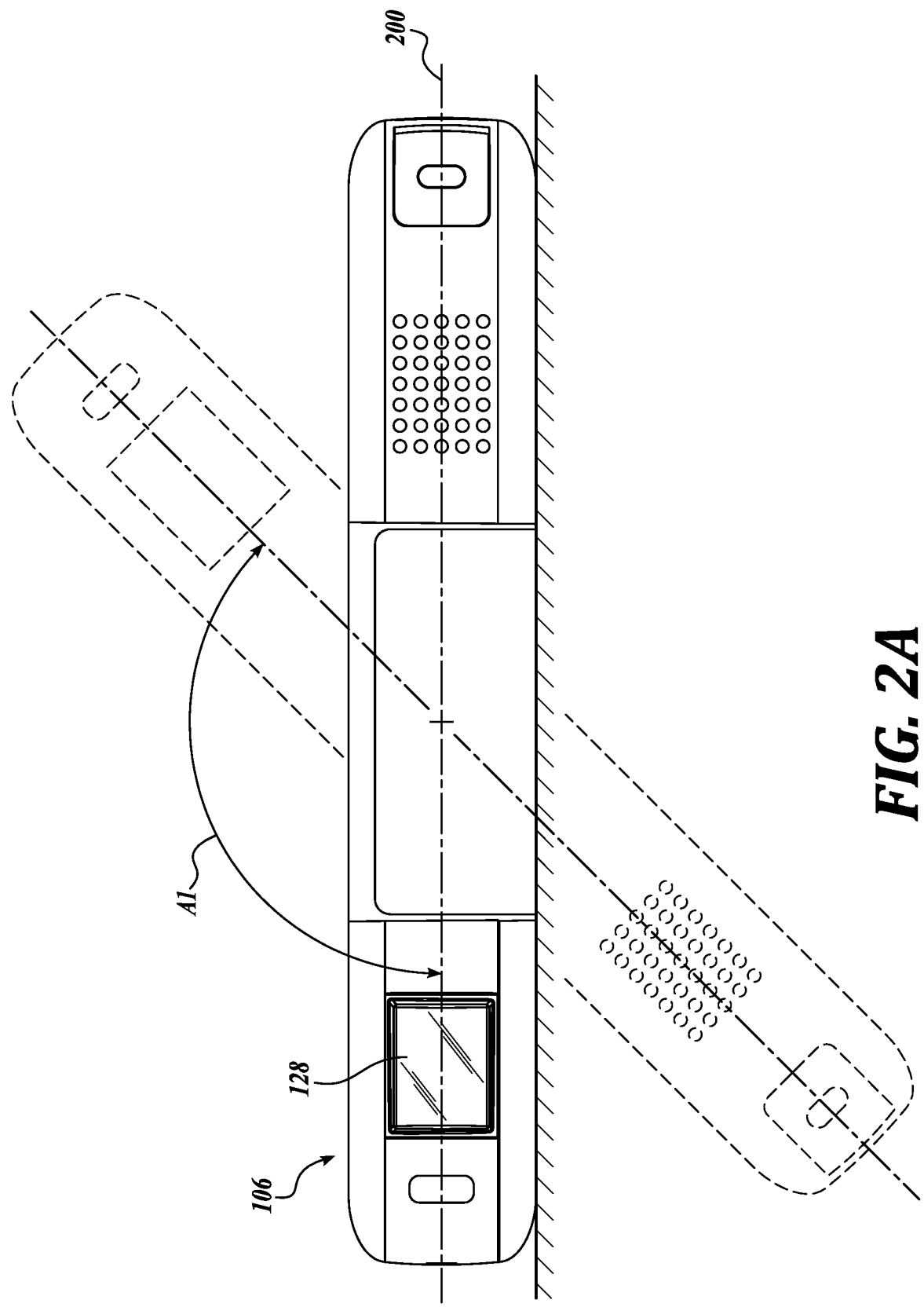
FIG. 2A and FIG. 2B are illustrations of an example of a communication device of the environment shown in FIG. 1 in accordance with one example of the present disclosure.
Figure 2B:
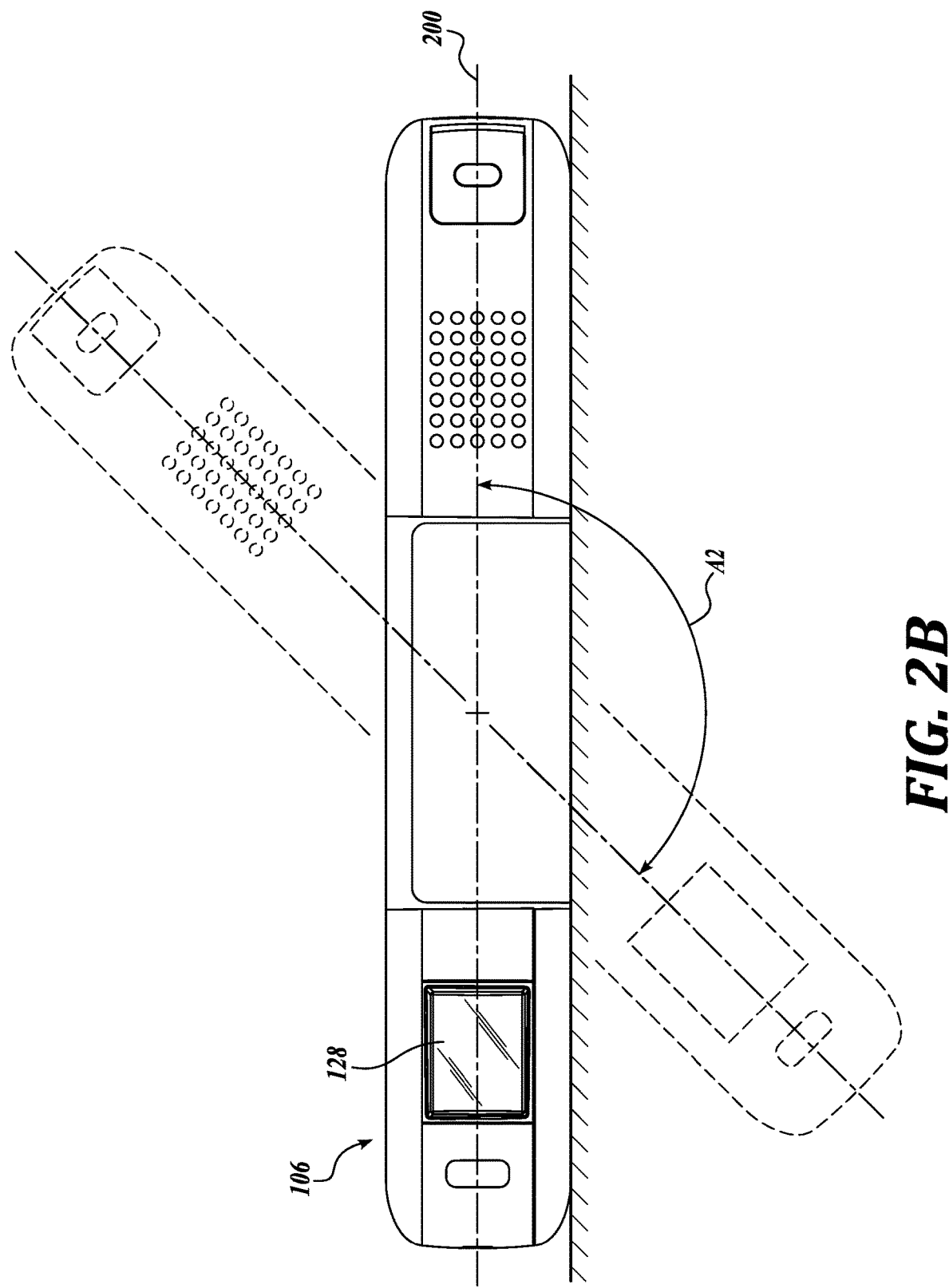

FIGS. 2A and 2B illustrate an example of the defibrillator 118 with a communication device 106 according to embodiments described herein. The defibrillator 118 may rest on along a plane 200. However, in this position of rest, the patient may not be able to view the communication device 106 clearly. For example, the screen (e.g. screen 128, FIG. 1) may be skewed or simply not in view. To see the communication device 106, the patient may rotate the defibrillator 118. This may cause the defibrillator to rotate either clockwise about angle A1 or counterclockwise about angle A2. As the defibrillator 118 rotates, the viewing angle of the communication device 106 also changes. The change in viewing angle may cause the patient to have a difficult time viewing information. Therefore, as the defibrillator 118 rotates, the screen 128 may also rotate or align the images and text projected to correlate to either viewing angle A1 or A2.

The threshold for altering the viewing angle may be a range of angles for angle A1 and angle A2. For example, the viewing angle may rotate when angle A1 or angle A2 ranges from 20 degrees to 60 degrees, 30 degrees to 50 degrees, or the like. A rotational range for angle A1 and angle A2 may prevent the screen from oscillating between various view orientations. For example, if the threshold was a strict degree threshold then the screen 128 may continuously alternate between viewpoints in an attempt to accommodate the shifting of the defibrillator 118 (e.g., a hysteresis-type effect). This may cause patient frustration in interacting with the device. However, some users may prefer a more sensitive display than others, therefore the threshold of view orientations may be personalized for the particular wearer of the WCD.

Figure 3:
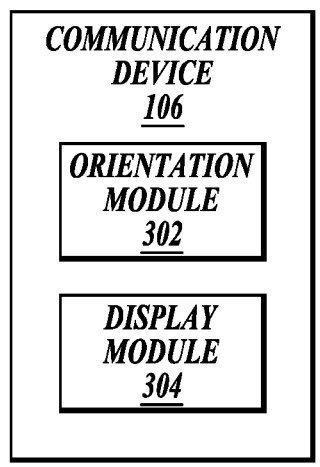
FIG. 3 is a diagram of an example of a communication device of the environment shown in FIG. 1 in accordance with one example of present disclosure.

FIG. 3 is a block diagram illustrating one example of a communication device 106. The communication device 106 may be coupled to the defibrillator 118 or may be a separate device. In this example, the communication device 106 has an orientation module 302 and a display module 304.

The patient may view the communication device 106 at various times throughout the day in various different orientations. The patient may view the communication device 106 in their dominant hand most of the time. However, the communication device 106 may not always be oriented properly such that a fixed screen would naturally appear to the user. If an alarm was sounding of an impending shock, or another warning signal, the user might get flustered viewing the screen on the communication device in a disorientating or non-normal manner. For example, the user may pick up the communication device 106 upside down or in a non-dominant hand. The disorientation may cause the user to fail to deactivate the defibrillation device and as such, an unnecessary and potentially damaging shock may be delivered to the patient.

Similarly, the patient may view the communication device 106 coupled to a defibrillation (e.g. defibrillator 118, FIG. 1). In these instances, the communication device 106 may be pointed away from the patient causing the patient to tilt the communication device 106 towards them. For that reason, any information displayed to the patient may be upside down or otherwise skewed. This may be true if the defibrillator 118 is coupled to the support structure or external to the support structure.

In some embodiments, the communication device 106 may be an LCD screen which may be coupled to the defibrillator 118 in such a manner that the screen is visible on a top side of the defibrillator 118.

Further, a third party may need to interact with the WCD system but, again, the communication device 106 may not orient properly for the third party. A patient may be unable to care for themselves and a nurse or family member or other individual may be providing care and may monitor the patient's health. A patient may require assistance should a cardiac event or accident arise.

Regardless of the situation, if the screen has a single orientation, at some point the screen will appear skewed, upside down, or otherwise unnatural to the viewer. In emergency or high stress situations, this may cause unnecessary delays, accidental inputs, further stress on the situation, and the like.

The orientation module 302 may help detect incorrect screen orientation or alignment. The orientation module 302 may receive information from one or more sensors proximate the communication device 106. The sensors may provide data readings involving the movement and orientation of the communication device 106. For example, one or more accelerometers proximate the communication device 106 may determine when the device 106 is moving and the speed at which it moves. The accelerometer may additionally detect tilt and vibrations. The data may provide feedback to determine when predetermined thresholds are met to detect movement of the device 106. Additionally, or alternatively, a gyroscope may provide further orientation details of the device 106. The orientation module 302 may pull and/or receive data from these sensors, individually or collaboratively, to determine when the device 106 is in use and desired orientation features associated with that use. For example, the orientation module 302 may determine a user is picking up the communication device 106 with their left or right hand based on the sensor feedback. The orientation module 302 may further determine when the communication device 106 is flat, tilted, jilted, vibrating, or otherwise orientation. The orientation module 302 may further determine when a third party is viewing the device. The orientation module 302 may further determine if the user is interacting with the communication device 106 either on a right side or left side of their body.

The display module 304 may receive orientation information from the orientation module 302 and activate a graphical user interface (GUI) associated with the device 106 as determined. For example, the display module 304 may rotate the content of the GUI to appear upright to the patient. The display module 304 may provide visual indication such as a light, or other visual indicator to indicate a status of the communication device 106 or the WCD system (e.g. WCD system 104, FIG. 1). In some embodiments, when motion is detected by the orientation module 302, the display module 304 may activate a backlight or a screen to provide increased visibility of the content to the patient or other user. As the orientation module 302 depicts movement of the communication device 106, the display module 304 may automatically activate at least a portion of the GUI. Activating a portion of the GUI may alert the patient to a status of the system, or other information.

In some embodiments, the patient may personalize the GUI to display criteria, parameters, or other information of important to the patient. For example, in some instances, the display module 304 may remember a preferred screen orientation. For example, the display module 304 may store patient preferences and remember whether the user wears the communication device 106 on either a left side or a right side of the body. The display module 304 may store this preference and automatically orient the communication device 106 to properly display to the user based on the user's preferences.

Figure 4:
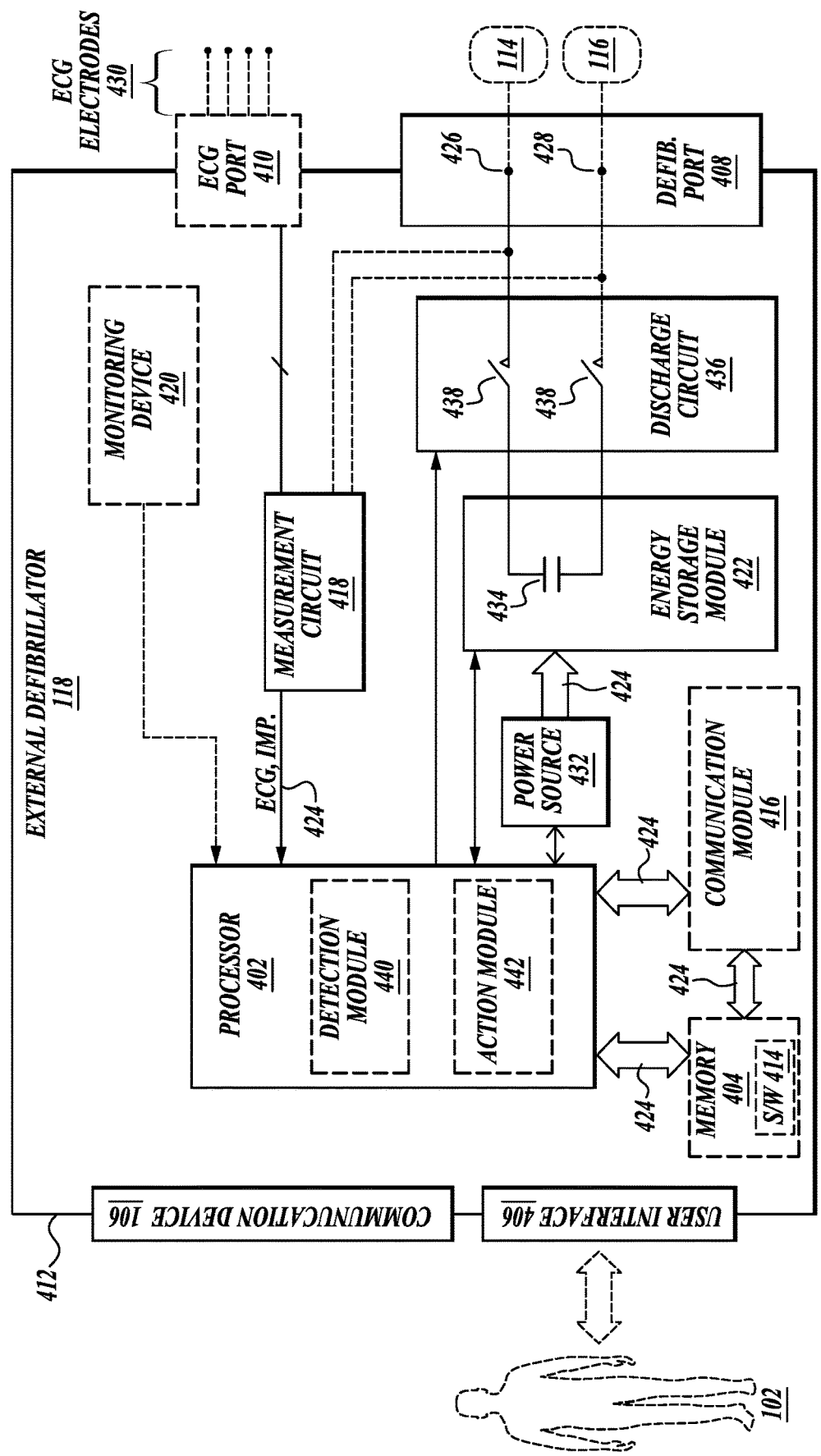
FIG. 4 is a block diagram of an example of a defibrillator unit of the environment shown in FIG. 1 in accordance with one example of the present disclosure.

FIG. 4 is a diagram displaying various functional components of one example of a defibrillator 118. The defibrillator 118 may be an example of the defibrillator 118 described with reference to FIG. 1. The components shown in FIG. 4 may be contained within a single unit or may be separated amongst two or more units in communication with each other. The defibrillator 118 may include a processor 402, memory 404, user interface 406, defibrillation port 408, and ECG port 410, among other components. In some embodiments, the components are contained within a housing 412 or casing. The housing 412 may comprise a hard shell around the components or may comprise a softer shell for increased patient comfort.

The processor 402, memory 404 (including software/firmware code (SW) 414), user interface 406, defibrillation port 408, ECG port 410, communication module 416, measurement circuit 418, monitoring device 420, and energy storage module 422 may communicate—directly or indirectly—with one another (e.g., via one or more buses 424). One or more buses 424 may allow data communication between one or more elements and/or modules of the defibrillator 118. In some embodiments, the communication device 106 may also communicate with the components of the defibrillator 118 using one or more buses 424. In some embodiments, the communication device 106 may replace the user interface 406. In still further embodiments, the communication device 106 may share components with the defibrillator 118 including the processor 402, memory 404, and the like.

The memory 404 may include random access memory (RAM), read only memory (ROM), flash RAM, and/or other types. The memory 404 may store computer-readable, computer-executable software/firmware code 414 including instructions that, when executed, cause the processor 402 to perform various functions (e.g., determine shock criteria, determine consciousness of patient, track patient parameters, etc.). In some embodiments, the processor 402 may include a with an intelligent hardware device, e.g., a central processing unit (CPU), a microcontroller, an application-specific integrated circuit (ASIC), etc.

In some embodiments, the memory 404 can contain, among other things, the Basic Input-Output system (BIOS) which may control basic hardware and/or software operations such interactions and workings of the various components of the defibrillator 118, and in some embodiments, components external to the defibrillator 118. For example, the memory 404 may contain various modules to implement the workings of the defibrillator 118 and other aspects of the present disclosure.

In some embodiments, the defibrillator 118 may include a user interface 406. In some embodiments, the user interface 406 may be a part of a communication device 106. The user interface 406 may enable the patient to view one or metrics concerning the defibrillator 118. For example, the user interface 406 may display an ECG of the patient, a status of the defibrillator 118, a status of a charge (e.g. a battery charge or an energy storage module). In some embodiments, the user interface 406 may be a simple configuration and a separate device, such as an electronics module (e.g. electronics module 104, FIG. 1).

In some embodiments, the defibrillator 118 may include a defibrillation port 408. The defibrillation port 408 may comprise a socket, opening, or electrical connection in the housing 412. In some instances, the defibrillation port 408 may include two or more nodes 426, 428. The two or more nodes 426, 428 may accept two or more defibrillation electrodes (e.g. defibrillation electrodes 114, 116, FIG. 1). The nodes 426, 428 may provide an electrical connection between the defibrillation electrodes 114, 116 and the defibrillator 118. The defibrillation electrodes 114, 116 may plug into the two or more nodes 426, 428 via one or more leads (e.g. leads 128), or, in some instances, the defibrillation electrodes 114, 116 may be hardwired to the nodes 426, 428. Once an electrical connection is established between the defibrillation port 408 and the electrodes 114, 116, the defibrillator 118 may be able to deliver an electric shock to the patient.

In some embodiments, the defibrillator 118 may include an ECG port 410 in the housing 412. The ECG port 410 may accept one or more ECG electrodes 430 or ECG leads. In some instances, the ECG electrodes 430 sense a patient's ECG signal. For example, the ECG electrodes 430 may record electrical activity generated by the heart muscle depolarization. The ECG electrodes 430 may utilize 4-leads to 12-leads or multichannel ECG, or the like. The ECG electrodes 430 may connect with the patient's skin.

In some embodiments, the defibrillator 118 may include a measurement circuit 418. The measurement circuit 418 may be in communication with the ECG port 410. For example, the measurement circuit 418 may receive physiological signals from ECG port 410. The measurement circuit 418 may additionally or alternatively receive physiological signals via the defibrillation port 408 when defibrillation electrodes 114, 116 are attached to the patient. The measurement circuit 418 may determine a patient's ECG signal from a difference in voltage between the defibrillation electrodes 114, 116.

In some embodiments, the measurement circuit 418 may monitor the electrical connection between the defibrillation electrodes 114, 116 and the skin of the patient. For example, the measurement circuit 418 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 118 may include an internal monitoring device 420 within the housing 412. The monitoring device 420 may monitor at least one local parameter. Local parameters may include physical state of the patient such as ECG, movement, heartrate, pulse, temperature, and the like. Local parameters may also include a parameter of the WCD (e.g. WCD 102), defibrillator 118, environmental parameters, or the like.

In some embodiments, a WCD (e.g. WCD 104) may include an internal monitoring device 420 and an external monitoring device (e.g. external monitoring device 124). If both monitoring devices 124, 420 are present, the devices 124, 420 may work together to parse out specific parameters depending on position, location, and other factors. For example, the external monitoring device 124 may monitor environmental parameters while the internal monitoring device 420 may monitor patient and system parameters.

In some embodiments, the defibrillator 118 may include a power source 432. The power source 432 may comprise a battery or battery pack, which may be rechargeable. In some instances, the power source 432 may comprise a series of different batteries to ensure the defibrillator 118 has power. For example, the power source 432 may include a series of rechargeable batteries as a prime power source and a series of non-rechargeable batteries as a secondary source. If the patient is proximate an AC power source, such as when sitting down, sleeping, or the like, the power source 432 may include an AC override wherein the power source 432 draws power from the AC source.

In some embodiments, the defibrillator 118 may include an energy storage module 422. The energy storage module 422 may store electrical energy in preparation or anticipation of providing a sudden discharge of electrical energy to the patient. In some embodiments, the energy storage module 422 may have its own power source and/or battery pack. In other embodiments, the energy storage module 422 may pull power from the power source 432. In still further embodiments, the energy storage module 422 may include one or more capacitors 434. The one or more capacitors 434 may store an electrical charge, which may be administered to the patient. The processor 402 may be communicatively coupled to the energy storage module 422 to trigger the amount and timing of electrical energy to provide to the defibrillation port 408 and, subsequently, the patient.

In some embodiments, the defibrillator 118 may include a discharge circuit 436. The discharge circuit 436 may control the energy stored in the energy storage module 422. For example, the discharge circuit 436 may either electrical couple or decouple the energy storage module 422 to the defibrillation port 408. The discharge circuit 436 may be communicatively coupled to the processor 402 to control when the energy storage module 422 and the defibrillation port 408 should or should not be coupled to either administer or prevent a charge from emitting from the defibrillator 118.

In some embodiments, the discharge circuit 436 may include on or more switches 438. The one or more switches 438 may include an H-bridge.

In some embodiments, the defibrillator 118 may include a communication module 416. The communication module 416 may establish one or more communication links with either local hardware and/or software to the WCD and defibrillator 118 or to remote hardwire separate from the WCD system. In some embodiments, the communication module 416 may include one or more antennas, processors, and the like. The communication module 416 may communicate wirelessly via radio frequency, electromagnetics, local area networks (LAN), wide area networks (WAN), virtual private networks (VPN), RFID, Bluetooth, cellular networks, and the like. The communication module 416 may facilitate communication of data and commands such as patient data, episode information, therapy attempted, CPR performance, system data, environmental data, and so on.

In some embodiments, the processor 402 may execute one or more modules. For example, the processor 402 may execute a detection module 440 and/or an action module 442. The detection module 440 may be a logic device or algorithm to determine if any or a variety thresholds are exceeded which may require action of the defibrillator 118. For example, the detection module 440 may receive and interpret all of the signals from the ECG port 410, the defibrillation port 408, the monitoring device 420, an external monitoring device, and the like. The detection module 440 may process the information to ensure the patient is still conscious and healthy. If any parameter indicates the patient may be experiencing distress or indicating a cardiac episode, the detection module 440 may activate the action module 442.

The action module 442 may receive data from the detection module 440 and perform a series of actions. For example, an episode may merely be a loss of batter power at the power source 432 or the energy storage module 422, or one or more electrodes (e.g., ECG electrodes, defibrillation electrodes) may have lost connection. In such instances, the action module 442 may trigger an alert to the patient or to an outside source of the present situation. If an episode is a health risk, such as a cardiac event, the action module 442 may begin a series of steps. This may include issuing a warning to the patient, issuing a warning to a third party, priming the energy storage module 422 for defibrillation, releasing one or more conductive fluids proximate defibrillation electrodes 114, 116, and the like.

Figure 5:
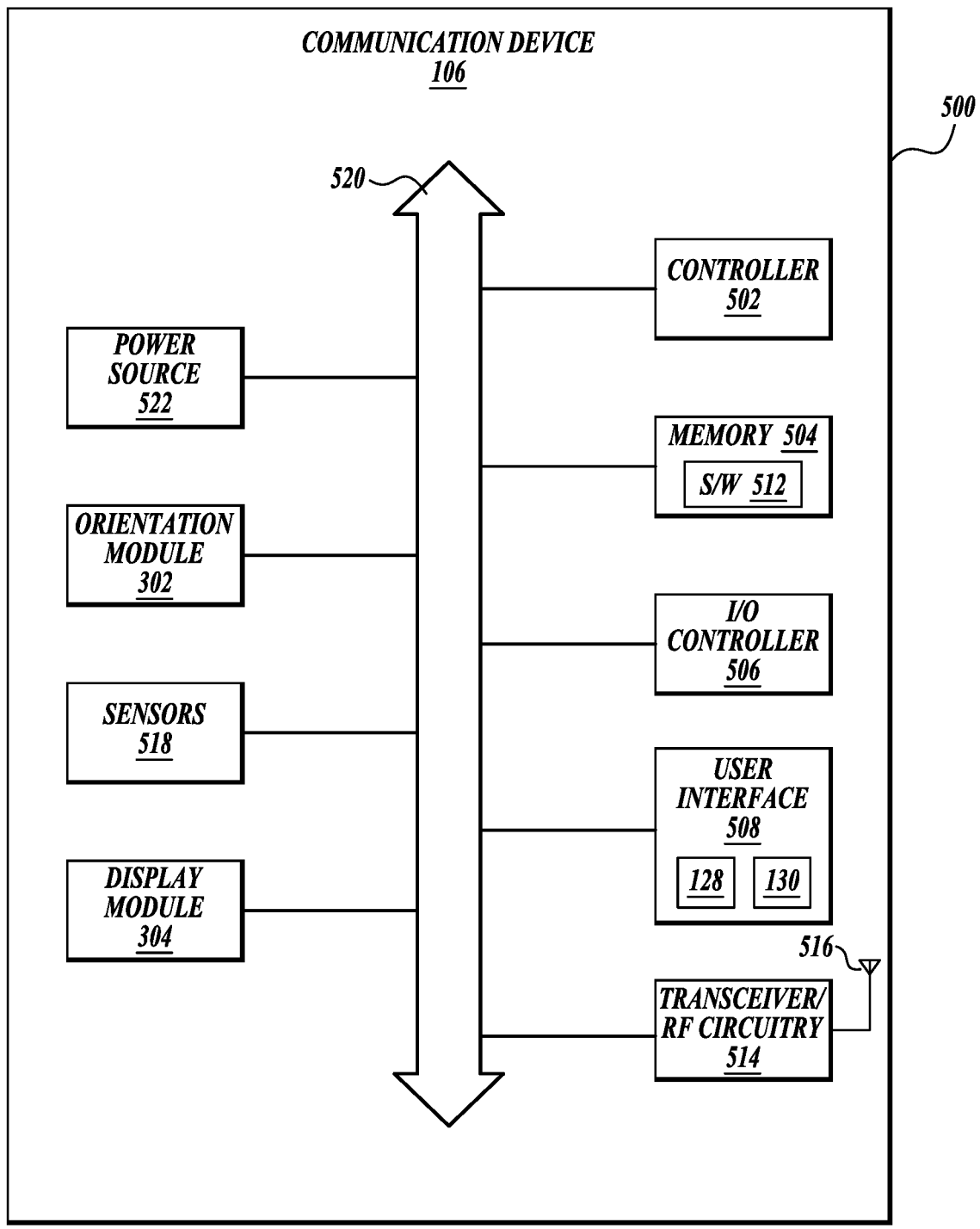
FIG. 5 is a block diagram of an example of a communication device of the environment shown in FIGS. 1 and 2 in accordance with one example of the present disclosure.

FIG. 5 is a diagram displaying various functional components of an example communication device 106 for use with a WCD system 104. The communication device 106 may be an example of the communication device 106 described with reference to FIG. 1. The communication device 106 may be a part of the defibrillator 118 or may be a separate device communicatively coupled to the defibrillator 118. The components shown in FIG. 5 may be contained within a single unit or may be separated amongst two or more units in communication with each other. In some embodiments, the communication device 106 may include a controller 502, memory 504, I/O controller 506, user interface 508, and the like. In some embodiments, the components are contained within a housing 500 or casing.

If the communication device 106 is a part of the defibrillator 118, the housing 500 may be integrated into the defibrillator 118. In further embodiments, if the communication device 106 is a part of the defibrillator 118, the communication device 106 may share components or functionality with the defibrillator 118. For example, the communication device 106 may use the processor 402 and memory 404 and other such components. In still further embodiments, the communication device 106 may be movable in relation to the defibrillator 118. For example, the communication device 106 may be linked or movably coupled to the defibrillator 118 about a pivot joint or the like. In still further embodiments, the communication device 106 may be removable from the defibrillator 118. In still further embodiments, the communication device 106 may be a separate device.

The controller 502, memory, 504 (including software/firmware code (SW) 512), input/output controller module 506, user interface module 508, transceiver module 514, and one or more antennas 516 may communicate—directly or indirectly—with one another (e.g., via one or more buses 520). The transceiver module 514 may communicate bi-directionally—via the one or more antennas 516, wired links, and/or wireless links—with the defibrillator 118 or remote devices 126 as described previously. The transceiver module 514 may include a modem which may modulate packets and provide the modulated packets to the one or more antennas 516 for transmission, and to demodulate packets received from the one or more antenna 516. While a single antenna 516 is shown, the communication device may include several antennas 516 which may concurrently transmit and/or receive multiple wired and/or wireless transmissions. In some embodiments, the communication device 106 may provide a connection using wireless techniques, including digital cellular connection, Cellular Digital Packet Data (CDPD) connection, digital satellite data connection, and/or another connection.

The controller 502 may control one or more operations of the communication device 106. The controller 502 may include of one or more processors, implemented as a Central Processing Unit (CPU), a digital signal processor, a microprocessor, a microcontroller, an application-specific integrated circuit (ASIC), a programmable logic device (PLD), or other implementation. In some embodiments, the controller 502 may include a single chip combined with memory controller and a peripherals interface.

The memory 504 may be a non-transitory computer-readable storage medium. In some embodiments, the memory 504 may include both persistent/non-volatile and non-persistent/volatile memory components. The memory 504 may include volatile memory, non-volatile memory (NVM), for example RAM, ROM, EEPROM, flash memory, or some combination thereof. The memory 504 may store computer-readable, computer executable software/firmware code 512 that, when executed, may cause the controller 502 to perform various functions as described herein.

In some embodiments, the memory 504 can contain, among other things, the Basic Input-Output system (BIOS) which may control basic hardware and/or software operations such interactions and workings of the various components of the communication device 106, and in some embodiments, components external to the communication device. For example, the memory 504 may contain various modules to implement the workings of the communication device 106 and other aspects of the present disclosure.

In some embodiments, the communication device 106 may include one or more sensors 518. The one or more sensor 518 may include orientation sensors, accelerometers, motion sensors, gyroscope, ambient light sensors, touchscreen sensors, magnetometer, sound sensors, or some combination thereof. An orientation sensor may measure the orientation of the communication device 106 relative to an orthogonal coordinate frame. An accelerometer may detect acceleration, vibration, and tilt to determine movement and exact orientation along the orthogonal coordinate frame. A gyroscope may provide further and/or additional orientation details and direction like up/down and left/right. The one or more sensors 518 may work in conjunction with the orientation module 302 and display module 304 to properly orient and wake a screen for the patient to interact with the communication device 106.

The user interface 508 may coordinate communication with the patient. For example, the user interface 508 may receive inputs from the user and also may generate outputs to the user. The outputs can be visual, sound, vibrations, lights, images, and so on. The user interface may include one or more individual devices such as a screen 128, touchscreen, a keypad 130, an optical finger interface, one or more speakers, one or more microphones, one or more accelerometers, one or more buttons, and so on.

The communication device 106 may also include components for bi-directional voice and data communications including components for transmitting communications and components for receiving communications. For example, the communication device 106 may communicate bi-directionally with the defibrillator 118, the WCD system 104, and/or external devices 124. The bi-directional communication may be direct or indirect.

The orientation module 302 may receive information from the one or more sensors 518 to determine movement or other inputs on the user interface 508. For example, the orientation module 302 may detect when there is a lack of movement and, as such, may put the user interface 508 into a sleep mode. The sleep mode may help preserve the battery life of the communication device 106, or if the communication device is a part of the defibrillator (e.g. defibrillator 118) preserve the battery of the defibrillator. The orientation module 302 may additionally detect when sudden movements or slower movements have occurred indicating the patient or a third party is interacting with the communication device 106.

The orientation module 302 may work in conjunction with a display module 304. The display module 304 may affect the changes requires in the visual interface between the patient and the user interface 508. For example, the display module 304 may rotate the visual display such that the display maintains an upright orientation to the user. This may include rotation about any pivot axis.

In some embodiments, the communication device 106 may include a power source 520. The power source 520 may comprise a battery or battery pack, which may be rechargeable. In some instances, the power source 520 may comprise a series of different batteries to ensure the communication device 106 has power. For example, the power source 520 may include a series of rechargeable batteries as a prime power source and a series of non-rechargeable batteries as a secondary source. If the patient is proximate an AC power source, such as when sitting down, sleeping, or the like, the power source 520 may include an AC override wherein the power source 520 draws power from the AC source.

Figure 6:
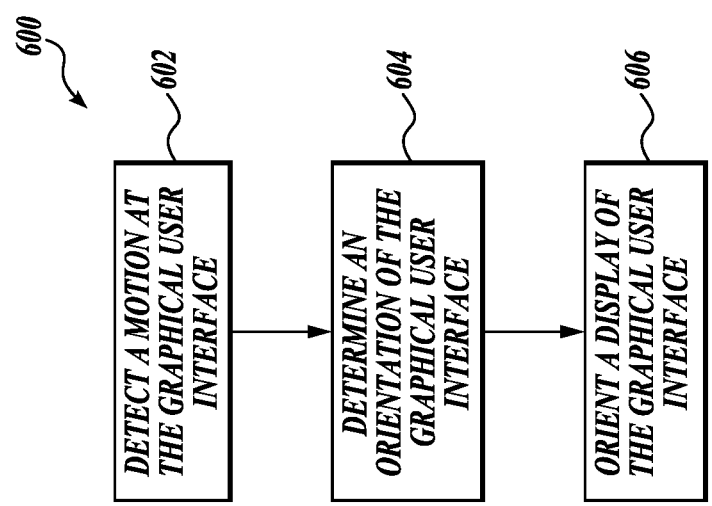
FIG. 6 is a flow diagram illustrating an example of a method for orienting a communication device in accordance with the present disclosure.

FIG. 6 is a flow chart illustrating an example of a method 600 for WCD systems, in accordance with various aspects of the present disclosure. For clarity, the method 600 is described below with reference to aspects of one or more of the systems described herein. In some examples, a separate communication device may perform one or more of the functions described below. In other embodiments, a communication device coupled to the defibrillator or the WCD system may perform one or more of the functions described below.

At block 602, the method 600 may include detecting a motion at a graphical user interface. The motion may be proximate a communication device or proximate a visual display coupled to the defibrillator unit. The motion may be a lateral motion, fixed-axis rotation, or may be a gyroscopic motion. The motion may be continuous and linear, or it may be sudden and uncontrolled, or it may be some combination of those.

At block 604, the method 600 may include determining an orientation of the graphical user interface based at least in part on the detection of a motion at the graphical user interface. For example, the method 600 may determine if a set threshold or threshold range has been satisfied or exceeded. The method 600 may compare the detected motion to specific user requirements on GUI orientation, or may compare the detected motion to general use profiles. In some embodiments, the method 600 may determine an action to take based on the type of motion. For example, the method 600 may determine if the user interface needs to be activated or turned on, if the user interface needs to be properly oriented, or if the user is interacting with the device using either their left hand or their right hand and a correlating user interface orientation. The method 600 may determine if the user interface needs to activate, be rotated, or if the user is interacting with the device with a specific hand, or the like.

At block 606, the method may include orienting a display of the GUI. For example, once motion is detected and determined, the method may proceed to properly orient the GUI or screen such that the patient or third party is properly viewing the screen in a better orientation.

Thus, the method 600 may provide for the communication device reacting to one or more movements or user inputs. It should be noted that the method 600 is just one implementation and that the operations of the method 800 may be rearranged or otherwise modified such that other implementations are possible.

Figure 7:
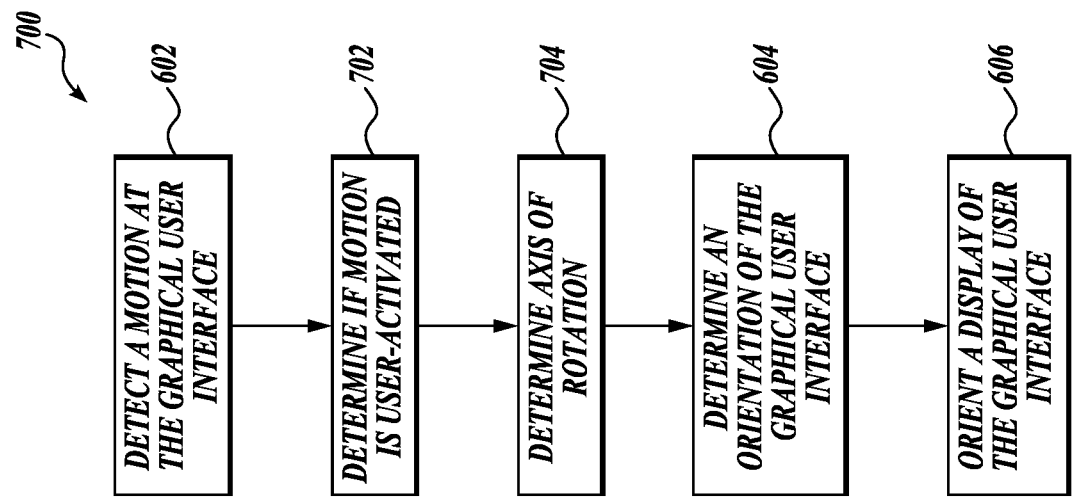
FIG. 7 is a flow diagram illustrating another example of a method for orienting a communication device in accordance with the present disclosure.

FIG. 7 is a flow chart illustrating an example of a method 700 for WCD systems, in accordance with various aspects of the present disclosure. For clarity, the method 700 is described below with reference to aspects of one or more of the systems described herein. In some examples, a separate communication device may perform one or more of the functions described below. In other embodiments, a communication device coupled to the defibrillator or the WCD system may perform one or more of the functions described below.

At block 602, the method 700 may include detecting a motion at a graphical user interface. At block 702, the method 700 may include determining if the motion is user-activated. For example, the motion may be a result of exercise, bodily movement, or other external actions or activities. Such motion may be continuous and linear or rhythmic, for example. If a patient accidently bumps the communication device, the sensors may detect motion but the motion may not be purposely induced. Such motion may be sudden and discontinuous, for example. Therefore, the method 700 may ascertain differences in movements between purposeful and environmental or accidental.

At block 704, if the movement was deliberate, the method 700 may include determining an axis of rotation and a directional vector. For example, if a user is purposefully interacting with the communication device, the method 700 may determine which axis the communication device is pivoting about and in which direction. The method 700, using this information, may then, at block 604, determine an orientation of the GUI and, at block 606, orient a display of the GUI.

Thus, the method 700 may provide for communication device reacting to one or more movements or user inputs. It should be noted that the method 700 is just one implementation and that the operations of the method 700 may be rearranged or otherwise modified such that other implementations are possible.

Figure 8:
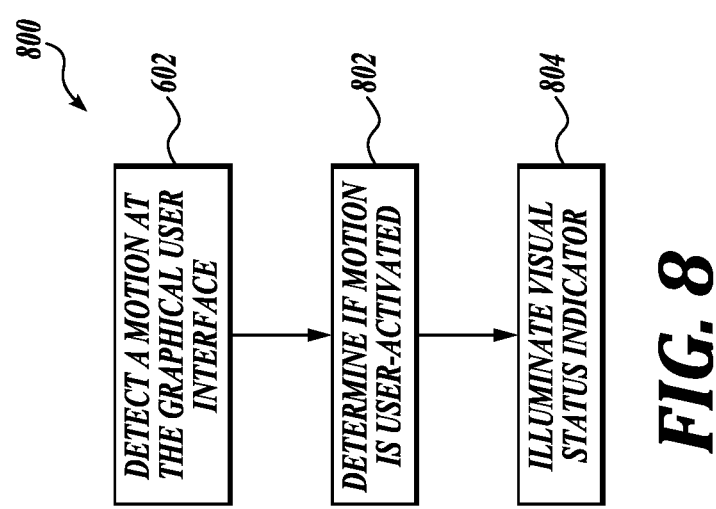
FIG. 8 is a flow diagram illustrating another example of a method for orienting a communication device in accordance with the present disclosure.

FIG. 8 is a flow chart illustrating an example of a method 800 for WCD systems, in accordance with various aspects of the present disclosure. For clarity, the method 800 is described below with reference to aspects of one or more of the systems described herein. In some examples, a separate communication device may perform one or more of the functions described below. In other embodiments, a communication device coupled to the defibrillator or the WCD system may perform one or more of the functions described below.

Again, at block 602, the method may include detecting a motion at a graphical user interface. At block 802, the method 800 may include determining if the motion is user-activated. At block 804, the method 800 may include illuminating a visual status indicator. For example, the user may have engaged the communication device to check a status of the WCD system. Therefore, the method 800 may provide visual feedback to the user of a status of the system. This may include illuminating various lights, such as LED lights, in different colors or in different orientations to display a status of the WCD system. The status indicators may include a status of a battery life, electrode connectivity, heart rate, and the like. The visual indicator may quickly indicate to the patient whether the WCD system is properly functioning without having to view a screen or further engage or interact with the WCD system.

Thus, the method 800 may provide for communication device reacting to one or more movements or user inputs. It should be noted that the method 800 is just one implementation and that the operations of the method 800 may be rearranged or otherwise modified such that other implementations are possible.

This document may include references to directions, such as "forward," "rearward," "front," "rear," "upward," "downward," "top," "bottom," "right hand," "left hand," "lateral," "medial," "in," "out," "extended," etc. These references, and other similar references, are only to assist in helping describe and to understand the particular embodiments and are not intended to limit the present disclosure to these directions or locations.

The present document may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

While illustrative embodiments have been illustrated and described, it will be appreciated that various changes can be made therein without departing from the spirit and scope of the disclosure.

We claim:

1. A system, comprising:
   a wearable cardioverter defibrillator (WCD) comprising:
      a support structure configured to be worn by a patient,
      one or more electrodes for delivering a charge to the patient,
      a discharge circuit coupled to the one or more electrodes for storing an electrical charge, and
      one or more processors configured to activate the discharge circuit, the one or more processors in communication with the discharge circuit; and
   a communication device configured to be communicatively coupled to the WCD, the communication device comprising:
      a user interface configured to receive inputs from a user and generate outputs to the user,
      a screen configured to display the user interface, and
      one or more sensors configured to orient and wake the screen for the patient to interact with the user interface of the communication device,
   wherein the communication device is configured to:
      detect a motion at the user interface via the one or more sensors,
      determine whether the motion is patient-activated,
      when the motion is not patient-activated:
         orient the content of the user interface to display the content based on one or more patient orientation preferences, and
      when the motion is patient-activated:
         determine an angle of rotation,
         determine that the angle of rotation exceeds a first angular threshold,
         determine an orientation of a display of the user interface, wherein a range of the orientation comprises a first range of angles that corresponds to the angle of rotation, the first range of angles comprises a first angle and a second angle, the first angle being greater than the second angle,
         orient content of the display of the user interface to correlate with the first range of angles when the angle of rotation exceeds the first angle, and
         maintain the orientation of the display when the angle of rotation falls below the first angle as long as the first angle of rotation exceeds the second angle.

2. The system of claim 1, wherein the communication device is a part of the WCD.

3. The system of claim 1, wherein the user interface has a baseline plane when the user interface is at rest.

4. The system of claim 1, wherein the communication device is further configured to:
   determine that the angle of rotation exceeds a second angular threshold,
   determine a second orientation of the display, wherein a range of the second orientation comprises a second range of angles that corresponds to the angle of rotation, and
   orient the content of the display to correlate with the second range of angles.

5. The system of claim 4, wherein at least one of the first and the second angular threshold is between 20 and 60 degrees from a baseline plane.

6. The system of claim 5, wherein at least one of the first and the second angular threshold is between 30 and 50 degrees from the baseline plane.

7. The system of claim 1, wherein the one or more sensors are further configured to determine an axis of rotation of the user interface.

8. The system of claim 1, wherein the angle of rotation is one of clockwise or counterclockwise.

9. The system of claim 1, wherein the communication device is further configured to provide a visual status indicator when the motion is patient-activated.

10. The system of claim 1, wherein the communication device is further configured to activate the user interface when the motion is patient-activated.

11. The system of claim 1, wherein the one or more sensors comprise:
    an orientation sensor configured to measure an orientation of the communication device relative to an orthogonal coordinate frame,
    an accelerometer configured to detect acceleration, vibration, and tilt to determine movement and orientation along the orthogonal coordinate frame,
    a gyroscope configured to provide orientation details and direction,
    an orientation module configured to receive information from the one or more sensors and to receive inputs from the user interface, and
    a display module configured to rotate the user interface such that the user interface maintains an upright orientation to the user,
    wherein the orientation sensor, the accelerometer, and the gyroscope are configured to work in conjunction with the orientation module and the display module.

12. A method of orienting the user interface of the communication device of claim 1, the method comprising:
    when the motion is user activated, determining an axis of rotation and a directional vector;
    determining an orientation of the user interface based, at least, on the detection of motion at the user interface; and
    orienting a display of the user interface, to allow the user to view the user interface.

13. The method of claim 12, wherein the motion is lateral motion, fixed axis rotation, or a gyroscopic motion.

14. The method of claim 12, further comprising:
    determining if a set threshold range has been met;
    comparing the detected motion to one or more user requirements of the user interface's orientation; and
    determining an action to be performed based on the type of motion.

15. The method of claim 14, wherein the action comprises activating the user interface, orienting the user interface, or correlating the user interface orientation based on whether a user is using left or right hand.

16. The method of claim 12, further comprising:
    determining if a set threshold range has been met;
    comparing the detected motion to a general use profile; and determining an action to be performed based on the type of motion.

17. The method of claim 12, further comprising:
illuminating a visual status indicator in response to the detected motion at the user interface.

18. The method of claim 17, wherein illuminating the visual status indicator comprises illuminating one or more LED lights in different colors and/or orientations.

19. The method of claim 17, wherein the visual status indicator comprises a status of battery life, electrode connectivity, or heart rate.

20. The method of claim 12, further comprising:
determining an angle of rotation,
determining that the angle of rotation exceeds a first angular threshold,
determining an orientation of a display of the user interface, wherein a range of the orientation comprises a first range of angles that corresponds to the angle of rotation, the first range of angles comprises a first angle and a second angle, the first angle being greater than the second angle,
orienting content of the display of the user interface to correlate with the first range of angles when the angle of rotation exceeds the first angle, and
maintaining the orientation of the display when the angle of rotation falls below the first angle as long as the first angle of rotation exceeds the second angle.

* * * * *